United States Patent
Fan et al.

(10) Patent No.: US 10,058,317 B2
(45) Date of Patent: Aug. 28, 2018

(54) KNOTLESS ANCHOR FOR INSTABILITY REPAIR

(71) Applicant: Smith & Nephew, Inc., Memphis, TN (US)

(72) Inventors: Wei Li Fan, Boston, MA (US); Amanda Simard, Hopkinton, MA (US)

(73) Assignee: Smith & Nephew, Inc., Memphis, TN (US)

( * ) Notice: Subject to any disclaimer, the term of this patent is extended or adjusted under 35 U.S.C. 154(b) by 268 days.

(21) Appl. No.: 14/417,399

(22) PCT Filed: Jul. 26, 2013

(86) PCT No.: PCT/US2013/052419
§ 371 (c)(1),
(2) Date: Jan. 26, 2015

(87) PCT Pub. No.: WO2014/018946
PCT Pub. Date: Jan. 30, 2014

(65) Prior Publication Data
US 2015/0201923 A1    Jul. 23, 2015

Related U.S. Application Data

(60) Provisional application No. 61/676,068, filed on Jul. 26, 2012.

(51) Int. Cl.
*A61B 17/04* (2006.01)

(52) U.S. Cl.
CPC .. *A61B 17/0401* (2013.01); *A61B 2017/0409* (2013.01); *A61B 2017/0412* (2013.01);
(Continued)

(58) Field of Classification Search
CPC .............. A61B 17/04; A61B 17/0401; A61B 2017/0409; A61B 2017/0414;
(Continued)

(56) References Cited

U.S. PATENT DOCUMENTS

2002/0161404 A1    10/2002  Steiner
2003/0120309 A1    6/2003   Colleran et al.
(Continued)

FOREIGN PATENT DOCUMENTS

EP    0829233 A1    3/1998
EP    1825817 A1    8/2007
WO    2007063285 A1    6/2007

OTHER PUBLICATIONS

International Preliminary Report for related PCT Application No. PCT/US2013/052419.
European Patent Office Communication from related European Application No. 13745770.1-1654 dated Jan. 3, 2017.

*Primary Examiner* — Jonathan Miles
*Assistant Examiner* — George J Ulsh
(74) *Attorney, Agent, or Firm* — Burns & Levinson, LLP; Joseph M. Maraia (57) ABSTRACT

Described herein are suture anchors systems and methods for installing suture anchor systems in bone. Suture anchor systems described herein include a plurality of annular ribs formed around an elongated cylindrical body, a tip adapted for inserting into a bone, one or more longitudinal channels defined by one or more notches in at least one of the annular ribs, and a transverse bore adapted to receive at least one suture and in communication with the longitudinal channel(s). The suture anchor system is partially inserted into the bone, the sutures are adjusted, and insertion is completed, securing the suture anchor and the suture in the bone.

18 Claims, 5 Drawing Sheets

(52) U.S. Cl.
CPC ............ *A61B 2017/0414* (2013.01); *A61B 2017/0437* (2013.01); *A61B 2017/0446* (2013.01); *A61B 2017/0451* (2013.01); *A61B 2017/0464* (2013.01)

(58) Field of Classification Search
CPC .... A61B 2017/0437; A61B 2017/0446; A61B 2017/0412; A61B 2017/0451; A61B 2017/0464; Y10T 24/00; Y10T 24/10; Y10T 24/13; Y10T 24/44274; Y10T 24/44282
USPC ........................................................ 606/232
See application file for complete search history.

(56) References Cited

U.S. PATENT DOCUMENTS

| | | | | |
|---|---|---|---|---|
| 2003/0225456 | A1* | 12/2003 | Ek | A61B 17/0401 623/20.14 |
| 2007/0203498 | A1* | 8/2007 | Gerber | A61B 17/0401 606/328 |
| 2007/0225719 | A1* | 9/2007 | Stone | A61B 17/0401 606/232 |
| 2010/0016902 | A1* | 1/2010 | Paulk | A61B 17/0401 606/300 |
| 2011/0112576 | A1 | 5/2011 | Nguyen et al. | |
| 2012/0078300 | A1 | 3/2012 | Mayer et al. | |

\* cited by examiner

KNOTLESS ANCHOR FOR INSTABILITY REPAIR

RELATED APPLICATIONS

This application is a U.S. national phase of International Application No. PCT/US13/052419, filed on Jul. 26, 2013. PCT/US13/052419 claims the benefit of U.S. Provisional Application No. 61/676,068, filed Jul. 26, 2012. The entirety of each of the aforementioned applications is incorporated by reference for all purposes.

BACKGROUND

Ball and socket joints in human appendages frequently undergo reconstructive surgery due to the high stress and movement demanded of the ball and socket bone structures. Often, such procedures involve surgical reattachment of labral tissue. The labral tissue, or labrum, is a type of soft tissue or cartilage that surrounds the socket of ball-and-socket joints, such as the shoulder and the hip joint. The labrum forms a ring around the edge of the bony socket of the joint, and helps to provide stability to the joint by deepening the socket, yet unlike bone, it also allows flexibility and motion.

SUMMARY

Labral reconstructive surgery often involves sutured reattachment of the labrum to the circumference of a socket joint. A knotless approach that secures the suture by a compression or friction fit of a suture anchor installed in a bone reduces both the number of surgical implants (parts) and the number of steps required of a surgeon in securing the labrum. An example of a knotless anchor includes ribs for compression resulting from insertion into a drilled surgical hole. The circumferential ribs employ discontinuous sections aligned to create a suture channel upon partial insertion in the surgical hole. The suture channel allows the suture to be drawn in tightening engagement with the labrum, and, in various example embodiments, secured by continuous circumferential rings as an upper (proximate) region of the anchor is driven into the hole, frictionally compressing the tightened suture between the continuous ring and the wall of the drilled hole.

In one aspect, at least one embodiment described herein provides a suture anchor. The suture anchor includes an elongated cylindrical body adapted for inserting into a bone. The suture anchor also includes a transverse bore at a distal portion of the elongated cylindrical body, the transverse bore adapted to receive at least one suture. The suture anchor also includes a plurality of annular ribs circumferentially formed around the elongated cylindrical body, the plurality of annular ribs including at least one discontinuous rib having at least one notch. The suture anchor also includes a channel defined by the at least one notch, the channel extending longitudinally through at least a portion of an outer surface of the suture anchor, the channel in communication with the transverse bore for receiving the suture.

Any of the aspects and/or embodiments described herein can include one or more of the following embodiments. In some embodiments the channel extends proximally from the transverse bore. In some embodiments the suture anchor also includes a cleat positioned along a length of the channel, adjacent to or within the transverse bore, wherein engaging the cleat with the suture arrests a slidable motion of the suture. In some embodiments at least one of the plurality of annular ribs is a continuous rib that continuously encircles the cylindrical body. In some embodiments the suture anchor also includes a distal tip configured to be inserted into bone without a surgical drill hole. In some embodiments the plurality of ribs taper from a first diameter at a proximal end of the elongated cylindrical body to a second diameter at the distal portion of the cylindrical body, the second diameter being smaller than the first diameter.

In some embodiments the suture anchor also includes a receptacle defined at a proximal end of the elongated cylindrical body, the receptacle configured for receiving an installation tool for driving the suture anchor into the bone. In some embodiments the receptacle has a cross-sectional shape selected from a group consisting of circular, triangular, square, hexagonal, polygonal and cross-shaped. In some embodiments at least a portion of the receptacle includes internal threads for receiving a threaded portion of the installation tool.

In one aspect, at least one embodiment described herein provides an anchor delivery system. The anchor delivery system includes any anchor described herein and an installation tool. The installation tool includes a handle and a drive shaft extending from the handle, the drive shaft configured for engaging with the receptacle.

Any of the aspects and/or embodiments described herein can include one or more of the following embodiments. In some embodiments the system includes at least one stay-suture connected to the anchor and the installation tool, the stay-suture configured to retain the anchor in operative engagement with the drive shaft of the installation tool. In some embodiments the handle includes at least one suture holder for holding one or more free ends of the at least one suture received by the transverse bore. In some embodiments at least a portion of the shaft includes external threads for engaging a portion of the receptacle having internal threads.

In one aspect, at least one embodiment described herein provides a method for securing a suture to bone without tying a knot. The method includes driving at least one discontinuous annular rib of an anchor into bone. The at least one discontinuous annular rib being circumferentially formed around a distal portion of the anchor. The method may also include adjusting the tension of at least one suture located within a transverse bore of the anchor. The tension of at the least one suture may be adjusted before or after driving the at least one discontinuous annular rib of the anchor into the bone. The method also includes after adjusting the tension of at least one suture, driving at least one continuous annular rib continuously encircling the anchor into bone to fix the anchor into the bone and to compress the suture between the bone and the at least one continuous annular rib securing the suture to the bone.

Any of the aspects and/or embodiments described herein can include one or more of the following embodiments. In some embodiments the step of driving the at least one discontinuous annular rib into bone includes engaging a distal end of an installation tool with a proximal end of the anchor. In some embodiments the step of driving the at least one discontinuous annular rib into bone also includes pounding the installation tool to drive the at least one discontinuous annular rib into the bone. In some embodiments the step of driving the at least one continuous annular rib into bone includes engaging a distal end of an installation tool with a proximal end of the anchor. In some embodiments the step of driving the at least one continuous annular rib into bone also includes pounding the installation tool to drive the at least one continuous annular rib into the bone.

In one aspect, at least one embodiment described herein provides a method for securing a suture to bone without tying a knot. The method includes driving at least one discontinuous annular rib of an anchor into bone. The at least one discontinuous annular rib being circumferentially formed around a distal portion of the anchor. The method may also include adjusting the tension of at least one suture located within a transverse bore of the anchor. The tension of at least one suture may be adjusted before or after driving the at least one discontinuous annular rib of the anchor into the bone. The method also includes after adjusting the tension of at least one suture, engaging the at least one suture with a cleat, wherein engaging the cleat arrests a slidable motion of the at least one suture.

Any of the aspects and/or embodiments described herein can include one or more of the following embodiments. In some embodiments the step of driving into bone the at least one discontinuous annular rib includes engaging a distal end of an installation tool with a proximal end of the anchor. In some embodiments the step of driving into bone the at least one discontinuous annular rib also includes pounding the installation tool to drive the at least one discontinuous annular rib into the bone. In some embodiments the step of engaging the at least one suture with a cleat further comprises pulling the at least one suture away from a distal end of the anchor.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
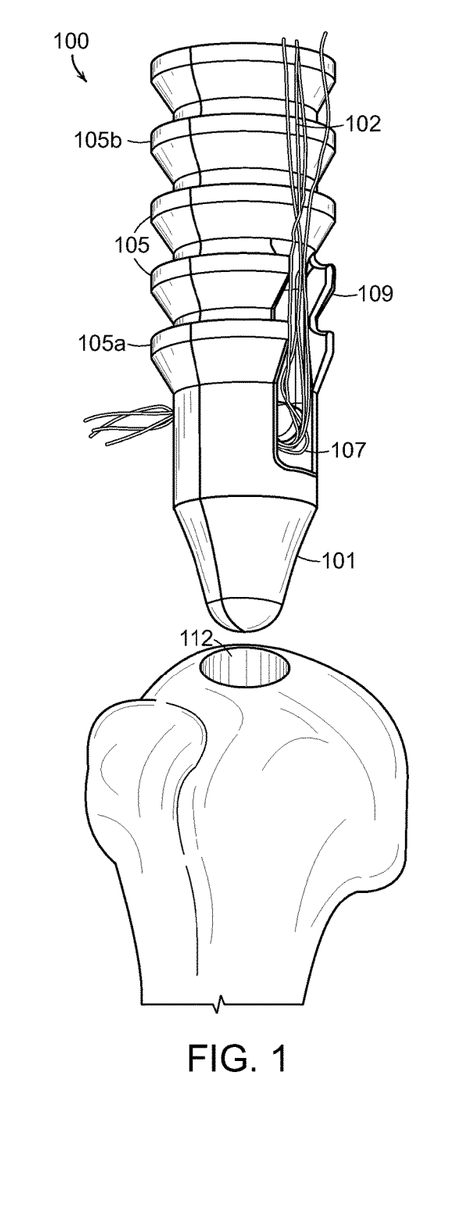
FIG. 1 shows a perspective view of a suture anchor in accordance with various embodiments.
Figure 2:
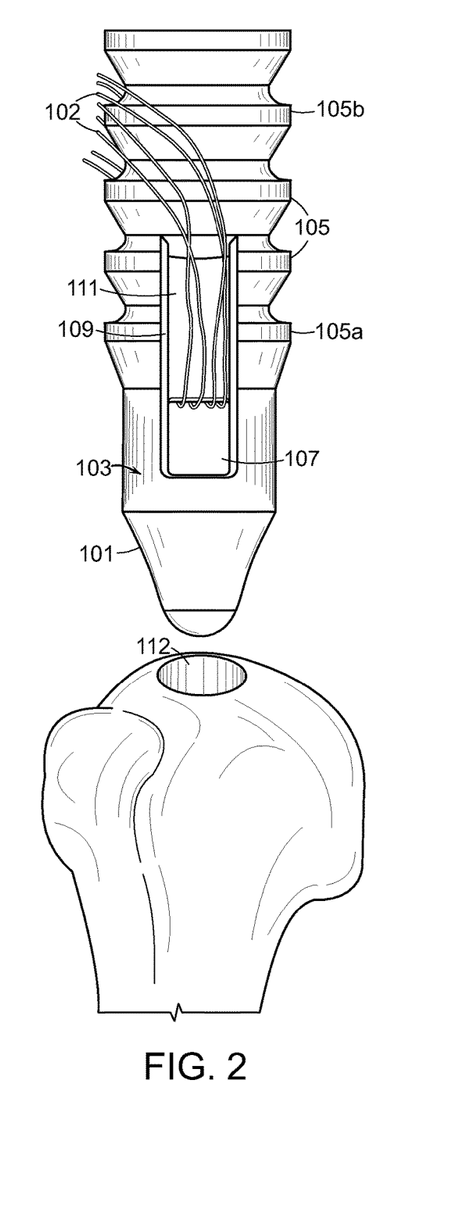
FIG. 2 shows a front elevation of the suture anchor of FIG. 1 in accordance with various embodiments.

FIGS. 1-2 show an example of a suture anchor 100 having a tip 101, an elongated cylindrical body 103, and a plurality of ribs 105 around the elongated cylindrical body 103, a transverse bore 107, and at least one longitudinal channel 111 defined by discontinuities 109 in the ribs 105. A surgeon applies an insertion force to the suture anchor 100 (e.g., with an inserter) to insert the tip 101, a distal portion of the elongated cylindrical body 103, and/or at least one of the plurality of ribs 105 into bone. Tension in the sutures 102 can then be adjusted by sliding sutures 102 in the transverse bore 107. Longitudinal channel(s) 111 allow free sliding of the suture(s) even when the suture anchor 100 is initially inserted deeper than the transverse bore 107. Then, the surgeon can insert the remaining portion of the suture anchor 100, including the remaining ribs 105, thereby compressing the ribs 105 against the bone to hold or "fix" the suture anchor 100 and/or the one or more sutures 102 within the bone.

Referring to FIGS. 1-5C, in accordance with various embodiments, a suture anchor 100, 300, 400, 500, 550 includes a tip 101 positioned at a distal end of an elongated cylindrical body 103, a plurality of annular ribs 105 formed circumferentially around the elongated cylindrical body 103 and stacked along a longitudinal length of the elongated cylindrical body 103. The suture anchor 100, 300, 400, 500, 550 also includes a transverse bore 107 for receiving one or more sutures 102, the transverse bore 107 positioned on a distal portion of the elongated cylindrical body 103. At least one of the annular ribs 105 includes one or more discontinuities or notches 109, thereby defining at least one longitudinal channel 111 in communication with the transverse bore 107 and extending proximally from the transverse bore 107. While any number of longitudinal channels 111 may be used, there will, in accordance with various embodiments, generally be two opposing longitudinal channels 111 defined by two opposing notches 109 in each discontinuous rib 105a. Some examples of the suture anchor 100, 300, 400, 500, 550 are made from a polymer (e.g., PEEK), composite (e.g., carbon fiber PEEK), or bioabsorbable materials. Other examples of the suture anchor are made from a combination of materials, as described below.

In accordance with various embodiments, the tip 101 can be integral with the elongated cylindrical body 103 or the tip 101 can be constructed separately and affixed to the distal end of the elongated cylindrical body 103. The tip 101 can be constructed of any suitable material, including for example, metal (e.g., surgical stainless steel or titanium), polymer (e.g., PEEK), composite (e.g., carbon fiber PEEK), or bioabsorbable materials. In various embodiments the tip 101 can advantageously be designed with the appropriate strength, stiffness, and shape (e.g., a pointed, conical, metal tip) for insertion into a bone 113 without the need for a surgical drill hole, referred to as a "no-hole-prep" tip. FIG. 5C shows an example of the suture anchor 550 in which the tip 101 is a "no-hole-prep" tip made titanium and the elongated cylindrical body 103 is made from carbon fiber PEEK. However, it will be apparent in view of this disclosure that, in accordance with various embodiments the tip 101 can be designed in a manner that the suture anchor 100, 300, 400, 500 can be inserted into a bone 113 after a surgical drill hole 112 has been provided. Such embodiments may include, for example, where the tip is advantageously constructed from bioabsorbables.

The annular ribs 105 are formed circumferentially around the elongated cylindrical body 103 and stacked along at least part of a longitudinal length of the elongated cylindrical body 103. In various embodiments, the annular ribs 105 are stacked along the entire longitudinal length of the elongated cylindrical body 103. However, it will be apparent in view of this disclosure that, in accordance with various embodiments, the annular ribs 105 are stacked along only a portion of the longitudinal length of the elongated cylindrical body 103. The cross-sectional shape of the annular ribs 105, in accordance with various embodiments, can include triangular, square, rectangular, trapezoidal, polygonal, circular, or any other suitable cross-sectional shape.

Figure 3:
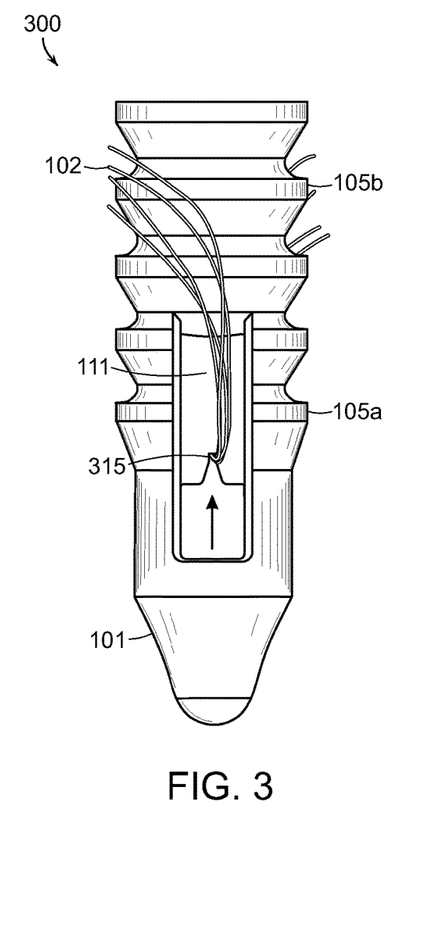
FIG. 3 shows front elevation of the suture anchor of FIG. 1 having a cleat in accordance with various embodiments.
Figure 4:
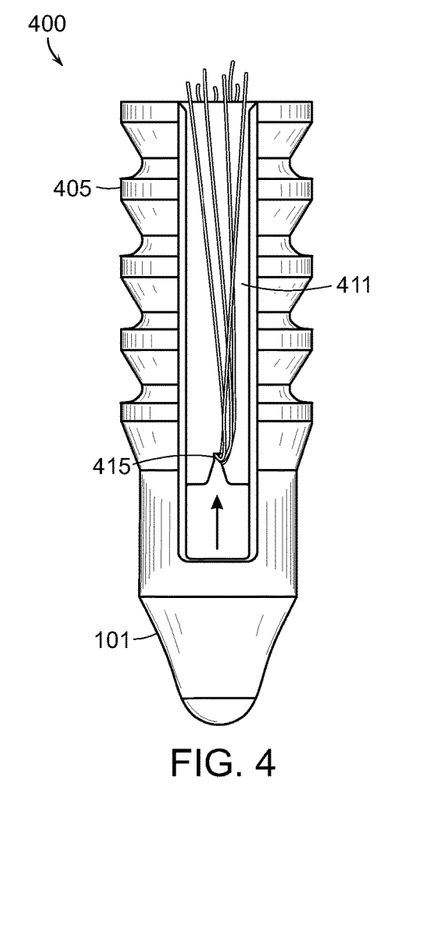
FIG. 4 shows a front elevation of an alternative suture anchor in accordance with various embodiments.

At least one of the annular ribs 105 includes one or more discontinuities or notches 109, thereby defining a longitudinal channel 111 in communication with the transverse bore 107 and extending proximally from the transverse bore 107. In a convenient example of the suture anchor, the notches 109 define two opposing longitudinal channel 111 that extend from either side of the transverse bore 107. In various embodiments (e.g., as shown in FIGS. 1-3 and 5A-5B) the suture anchor 100, 300, 500, 550 can include one or more discontinuous ribs 105a (i.e. ribs having at least one notch 109) and one or more continuous ribs 105b (i.e., ribs not having a notch 109). In various embodiments (e.g., as shown in FIG. 4) the suture anchor 400 includes only discontinuous ribs 405.

In accordance with various embodiments, a surgeon can partially insert the suture anchor 100, 300, 400, 500, 550 into bone, including at least one rib 105 to compress the at least one rib 105 against the bone and temporarily hold the suture anchor 100, 300, 400, 500, 550 in the bone. After the temporary hold is established, the surgeon can slide the one or more sutures 102 in the transverse bore 107 to adjust, for example, tension on the one or more sutures 102. When the adjustments are complete, the surgeon can complete insertion of the suture anchor 100, 300, 400, 500, 550 by driving the remaining ribs 105 into the bone to provide a more permanent fixation of the suture anchor 100, 300, 400, 500, 550 in the bone.

In various embodiments, the partial insertion reaches a depth such that the transverse bore 107 is below the surface of the bone. In such embodiments, sutures 102 positioned to transition out of the transverse bore 107 into the longitudinal channel(s) 111 will remain slidable and therefore adjustable until they are fixed by some other means. In accordance with various embodiments, the sutures 102 can be positioned to be compressed between one or more ribs 105 and the bone to arrest the slidable motion of the sutures 102. In accordance with various embodiments, the slidable motion of the sutures 102 can be arrested by engaging the sutures 102 with a cleat 315, 415 as further described below.

In various embodiments, the annular ribs 105 taper from a first rib diameter at a proximal portion of the elongated cylindrical body 103 to a smaller, second rib diameter at a distal portion of the elongated cylindrical body 103. The taper may, in various embodiments, reduce the force required to insert the suture anchor 100, 300, 400, 500, 550 into bone, reducing the risk of unwanted bone damage. Where a surgical drill hole 112 is desirable, in accordance with various embodiments, the diameter of at least one of the annular ribs 105 is sized for compressive fitting in a predetermined diameter of the surgical drill hole 112.

Transverse bore 107 is formed in a distal portion of the elongated cylindrical body 103 and is sized to accommodate one or more sutures 102. The transverse bore is in communication with the one or more longitudinal channels 111, which are defined by the notches 109 in the discontinuous ribs 105a. Each of the one or more longitudinal channels 111 is, in accordance with various embodiments, sized to accommodate at least one suture 102 therein. In some examples, the one or more sutures 102 are threaded through the transverse bore 107 as the suture anchor 100, 300, 400, 500, 550 is being inserted into bone. In other examples, the one or more sutures 102 are already threaded through the transverse bore 107 (i.e., preloaded) prior to the suture anchor 100, 300, 400, 500, 550 being inserted into bone. A "preloaded" example of the anchor is advantageous because a surgeon or other surgical member does have not to load a suture into the anchor themselves, which may be time consuming and/or laborious, particularly, when the anchor is small in size.

In various embodiments, the one or more longitudinal channels 111 extend longitudinally from the transverse bore 107 through at least a portion of an outer surface of the suture anchor, thereby forming the discontinuity/notch 109 in the one or more annular ribs 105. It will be apparent in view of this disclosure that a depth of the one or more longitudinal channels 111 can, in accordance with various embodiments, be constant or vary along an axial length of each longitudinal channel 111. It will be further apparent in view of this disclosure that the depth of each longitudinal channel 111 may be deeper than a height of the discontinuous ribs 105a, 405 and therefore impinge on an exterior of the cylindrical body 103 as well. While any number of longitudinal channels 111 may be used, there will, in accordance with various embodiments, generally be two opposing longitudinal channels 111 defined by two opposing notches 109 in each discontinuous rib 105a. The longitudinal channels 111, 411 can, in various embodiments, extend along the entire longitudinal length between the transverse bore 107 and the proximal end of the suture anchor 100, 300, 400, 500, 550 (e.g., as shown in FIG. 4) or, in various embodiments, the longitudinal channels 111, 411 can extend along only a portion of the longitudinal length (e.g., as shown in FIGS. 1, 2, 3, and 5A-5C).

In accordance with various embodiments, the suture anchor 300, 400 includes a cleat 315, 415 positioned along a length of the longitudinal channel 111, adjacent to the transverse bore 107, or within the transverse bore 107. Engaging the cleat 315, 415, in accordance with various embodiments, arrests a slidable motion of the suture(s). As shown in FIGS. 3 and 4, the cleat 315, 415 can be engaged by the one or more sutures 102 received by the transverse bore 107 by, for example and without limitation, pulling the suture(s) away from the distal end of the suture anchor 300, 400. In various such embodiments, the suture is moved proximal from the transverse bore 107 into a narrow opening or slot such that the suture is "pinched" or compressed within the narrow opening or slot, thereby arresting a slidable motion of the suture. The cleat 315, 415 can, in various embodiments, be advantageously used to secure the sutures 102 during at least part of the installation of the suture anchor 300, 400 into bone. As illustrated by FIGS. 3 and 4, a cleat 315, 415 can be used with embodiments having full-length longitudinal channels 411 or embodiments having partial-length channels 111.

Figure 5A:
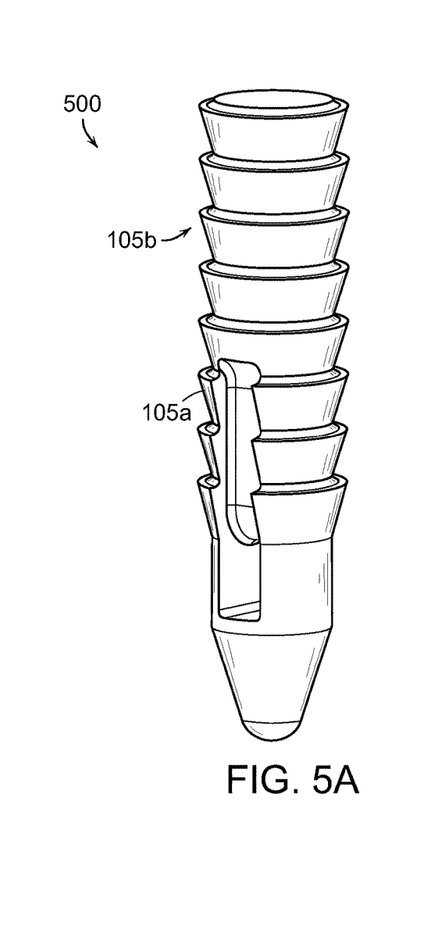
FIGS. 5A-5B show perspective and cross-sectional views of a suture anchor having a threaded receptacle in accordance with various embodiments.
Figure 5B:
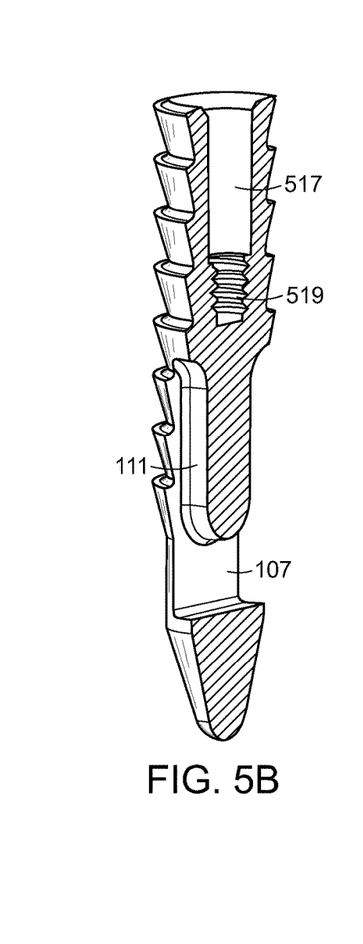
Figure 5C:
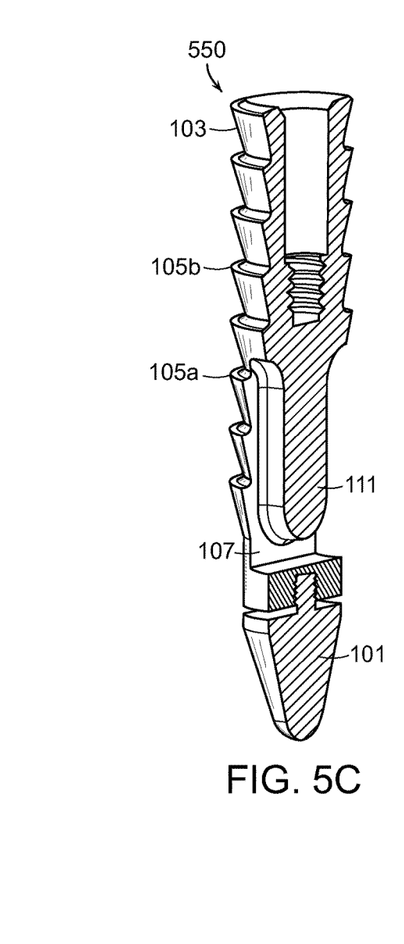
FIG. 5C shows a perspective view of a suture anchor having a no-hole-prep tip in accordance with various embodiments.

Referring now to FIGS. 5A and 5B, a suture anchor, in accordance with various embodiments can include a receptacle 517 for engaging an insertion tool. In various embodiments, the receptacle 517 can be an internal cavity defined by a proximal end of the suture anchor 500. The receptacle 517 can be constructed to include any suitable cross-sectional shape (e.g., circular, triangular, hexagonal, polygonal and cross-shaped).

The receptacle 517, in accordance with various embodiments, includes internal threads 519 for mating with external threads of the inserter. Thus the internal threads are configured to removably retain the suture anchor 500 in engagement with the inserter. In various embodiments, one or more stay sutures is passed through the transverse bore 107 and releasably attached to the inserter (e.g., at a suture holder feature of the inserter) to removably retain the suture anchor 500 in engagement with the inserter. In still other embodiments, the inserter includes projections that are engagable with corresponding grooves or recesses in the inner surface/wall of the receptacle 517 for a bayonet-type fit.

The inserter can, for example but not limited to, include a distal end having a shaft for engaging the receptacle 517 and a proximal end having a handle concentric with the shaft. In various embodiments, the handle further includes one or more suture-holding grooves (or suture-holders) formed into the handle.

Figure 6:
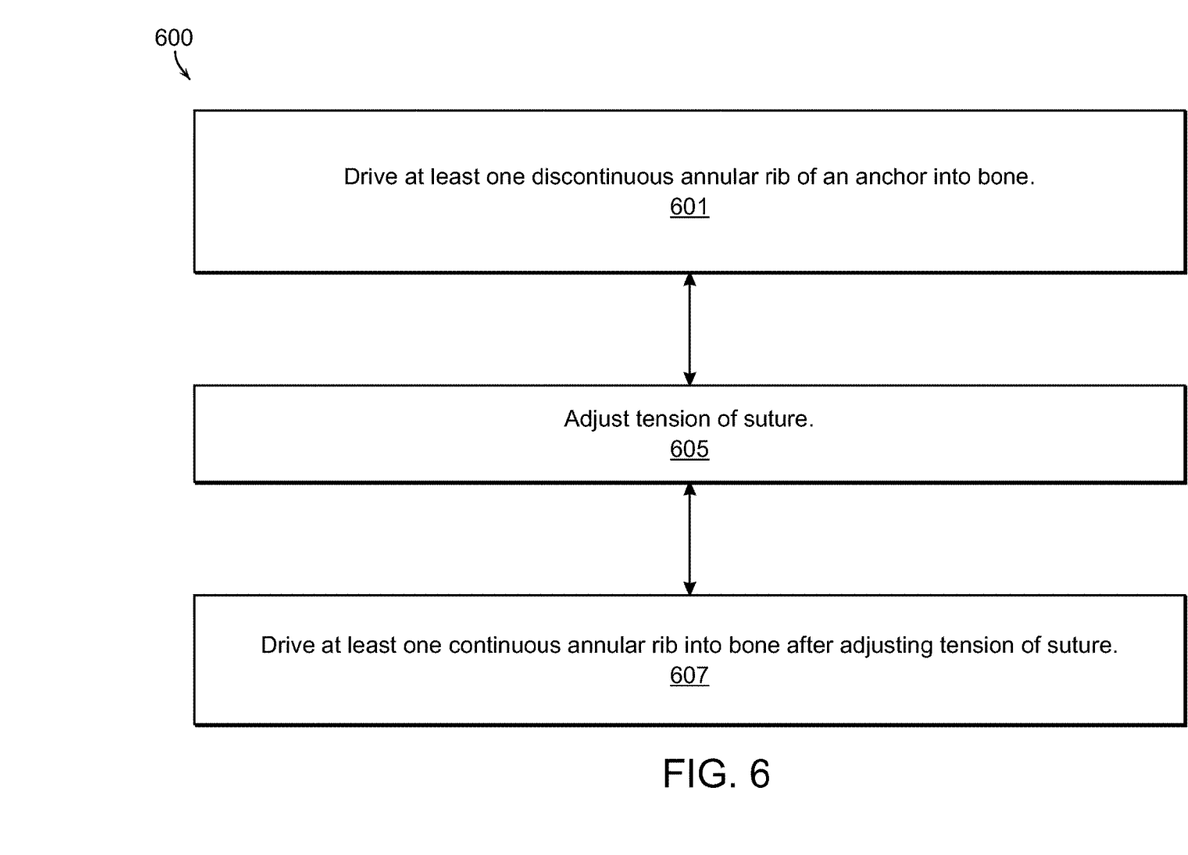
FIG. 6 shows a flow chart illustrating a method for securing a suture to bone in accordance with various embodiments.

Referring now to FIG. 6, a method for securing a suture to bone without tying a knot can include driving at least one discontinuous annular rib of an anchor into bone 601. The at least one discontinuous annular rib being circumferentially formed around a distal portion of the anchor. The method further includes adjusting (increasing or decreasing) the tension of at least one suture 605 located within the transverse bore 107. In some examples of the method, suture tension one is adjusted (605) before driving the discontinuous annular rib into bone (601). In other examples of the method, suture tension is adjusted (605) after driving the discontinuous annular rib into bone (601). The method further includes, after adjusting the tension of at least one suture (605), driving at least one continuous annular rib continuously encircling the anchor into bone to fix the anchor into the bone and to compress the suture between the bone and the at least one continuous annular rib securing the suture to the bone 607.

The step of driving at least one discontinuous annular rib of an anchor into bone 601 can, for example but not limited to, include using the inserter to install discontinuous ribs 105*a*, 405 of a suture anchor 100, 300, 400, 500, 550 into bone as described above with reference to any of FIGS. 1-5C.

The step of adjusting the tension of at least one suture 605 can, for example but not limited to, include sliding the suture(s) in the transverse bore 107 of the suture anchor 100, 300, 400, 500, 550 as described above with reference to any of FIGS. 1-5C. The step of adjusting suture tension can also include sliding the suture along a longitudinal channel, which was described above with reference to FIGS. 1-5C.

The step of driving at least one continuous annular rib continuously encircling the anchor into bone to fix the anchor into the bone and to compress the suture between the bone and the at least one continuous annular rib securing the suture to the bone 607 can, for example but not limited to, include using the inserter to install continuous ribs 105*b* of a suture anchor 100, 300, 500, 550 into bone as described above with reference to any of FIGS. 1-3, and 5A-5C.

Figure 7:
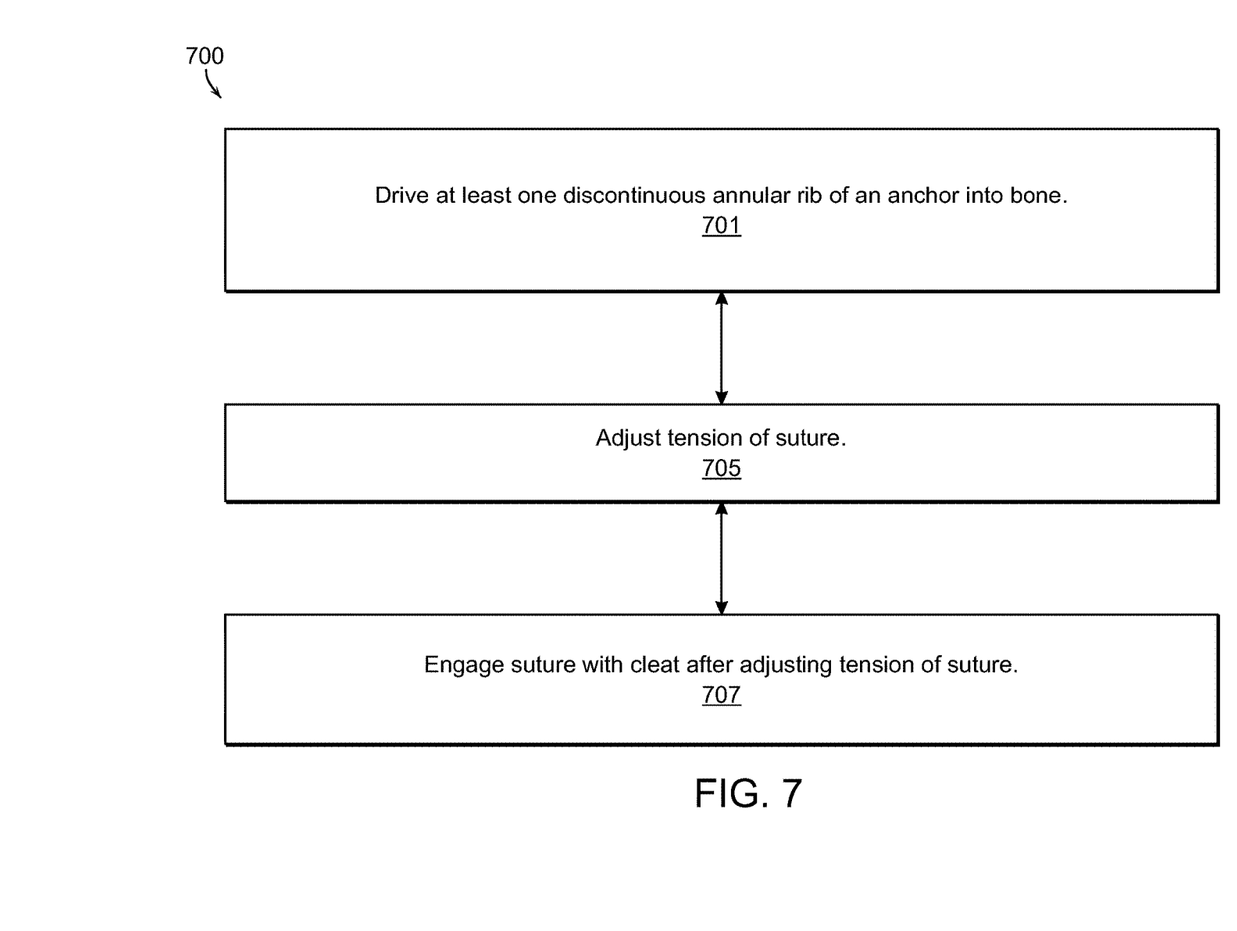
FIG. 7 shows a flow chart illustrating an alternative method for securing a suture to bone in accordance with various embodiments.

Referring now to FIG. 7, a method for securing a suture to bone without tying a knot can include driving at least one discontinuous annular rib of an anchor into bone. The at least one discontinuous annular rib being circumferentially formed around a distal portion of the anchor 701. The method further includes adjusting (increasing or decreasing) the tension of at least one suture 705 located within the transverse bore 107. In some examples of the method, suture tension one is adjusted (705) before driving the discontinuous annular rib into bone (701). In other examples of the method, suture tension is adjusted (705) after driving the discontinuous annular rib into bone (701). The method further includes, after adjusting the tension of at least one suture (705), engaging the at least one suture with a cleat, wherein engaging the cleat arrests a slidable motion of the at least one suture 707.

The step of driving at least one discontinuous annular rib of an anchor into bone 701 can, for example but not limited to, include using the inserter to install discontinuous ribs 105*a*, 405 of a suture anchor 100, 300, 400, 500, 550 into bone as described above with reference to any of FIGS. 1-5C.

The step of adjusting the tension of at least one suture 705 can, for example but not limited to, include sliding the suture(s) in the transverse bore 107 of the suture anchor 100, 300, 400, 500, 550 as described above with reference to any of FIGS. 1-5C. The step of adjusting suture tension 705 can also include sliding the suture along a longitudinal channel, which was described above with reference to FIGS. 1-5C.

The step of engaging the at least one suture with a cleat, wherein engaging the cleat arrests a slidable motion of the at least one suture 707 can, for example but not limited to, include engaging the suture(s) with a cleat 315, 415 as described above with reference to FIGS. 3 and 4.

The foregoing methods can also include threading the at least one suture through the transverse bore of the anchor (not shown). The step of threading at least one suture through a transverse bore of the anchor, in accordance with various embodiments, includes inserting one or more sutures 102 into a transverse bore 107 of a suture anchor 100, 300, 400, 500, 550. It will be apparent in view of this disclosure that the step of threading can be performed before or during insertion of the suture anchor 100, 300, 400 500, 550. For example, the suture(s) can be preloaded onto the anchor by a manufacturer, the suture(s) can be threaded by a surgeon prior to any insertion, and/or the suture(s) can be threaded after partial insertion of the anchor but prior to the surgeon slidably adjusting a tension in the suture.

EXAMPLE

In one example embodiment, the suture anchor includes an eyelet at a tapered end of a 2.3 mm diameter anchor. Referring to FIGS. 1 and 2, annular ribs (circumferential rings) 105 disposed along the anchor are sized for compressive fitting in a surgical drilled hole 112 of a predetermined diameter, and include continuous ribs 105*b* and discontinuous ribs 105*a*. The discontinuous ribs 105*a* form a longitudinal suture channel 111 at the distal (tapered) end of the anchor 100 inserted into the drilled hole 112. The suture channel 111 is in communication with one or more transverse bores (eyelets) 107 adapted for receiving a suture therethrough. The suture channel 111 is defined by the discontinuous portion 109 of the most distal ribs 105*a* disposed at the tapered end. In the example configuration, the suture channel 111 and eyelet 107 are widened to fit two strands of sutures 102, and the suture channel 111 is only apparent in the distal two ribs. The last (most proximate) ribs 105*b* have a full diameter (i.e. are continuous), and are adapted to a procedure as follows:

1) The distal rib(s) 105*a* of the anchor are driven into the bone (drilled hole 112) via a hammering receptacle (e.g., 517) at the proximate end.

2) The suture is adjusted so that there is a small amount of slack corresponding to the remaining depth to be driven for the continuous rings 105*b*.

3) The rest of the anchor 100 is pounded into the bone enabling fixation of the anchor 100 into the drilled hole 112 and the suture is pinched or compressed against the bone (e.g., sides of hole 112) fixing the suture and preventing movement.

In the example arrangement, the suture forms a loop of which both strands extend through the eyelet 107.

FIG. 4 shows an alternate configuration of the suture anchor of FIG. 1. Referring to FIG. 4, a cleat 415 secures the suture, and the channel 111 extends the length of the anchor 100 due to all discontinuous circumferential rings 405.

Advantages over conventional approaches include a single component design, fewer installation steps, and no turning (i.e. screwing or rotating a threaded securement mechanism) is required.

In the example arrangement, the knotless surgical anchor 100 includes an elongated cylindrical body 103 adapted for inserting into a surgical drill hole 112, and a transverse bore defining the eyelet 107 at a distal end of the cylindrical body 103, in which the transverse bore 107 is adapted to receive at least one suture thread. A plurality of annular ribs 105 are circumferentially formed around the elongated cylinder, and a longitudinal suture channel 111 is defined by a discontinuity 109 in the annular ribs 105a running axially along the cylinder 103, such that at least one of the annular ribs 105b continuously encircles the cylinder, in which the longitudinal channel 111 is in communication with the transverse bore 107 for receiving the suture thread.

For the labral tissue procedure described, the suture thread is a suture loop having two strands extending through the transverse bore. In the example arrangement, the cylindrical body 103 has a tapered area of reducing diameter at the distal end and a receptacle 517 at a proximate end, the receptacle for receiving an installation tool for driving the cylindrical body 103 into the surgical drill hole 112. The continuous annular rings 105b therefore define the discontinuity 109 in the longitudinal suture channel 111, such that each of the discontinuous ribs 105a is disposed in an aligned sequence at the distal end for forming the channel 111, in which each of the continuous annular rings 105b is disposed consecutively at the proximate end.

What is claimed is:

1. A suture anchor comprising:
   an elongated cylindrical body adapted for inserting into a bone, a longitudinal axis of the elongated body extending between distal and proximal ends thereof;
   a transverse bore at a distal portion of the elongated cylindrical body, the transverse bore adapted to receive at least one suture;
   a plurality of ribs circumferentially formed around the elongated cylindrical body closer to the proximal end than the transverse bore, the plurality of ribs including at least one discontinuous rib having at least one notch and at least one continuous rib that continuously encircles the cylindrical body, wherein the at least one continuous rib is closer to the proximal end than the at least one discontinuous rib;
   a longitudinal channel defined by the at least one notch, the longitudinal channel extending proximally from the transverse bore through a portion of an outer surface of the suture anchor, the longitudinal channel in communication with the transverse bore for receiving the suture; and
   a cleat defining a narrow opening or slot configured to engage the at least one suture within the narrow opening or slot, wherein the cleat is positioned along a length of the longitudinal channel adjacent to the transverse bore; such that engaging the cleat with the at least one suture arrests a slidable motion of the at least one suture.

2. The suture anchor of claim 1, further comprising a distal tip configured to be inserted into bone without a surgical drill hole.

3. The suture anchor of claim 1, wherein the plurality of ribs taper from a first diameter toward the proximal end of the elongated cylindrical body to a second diameter toward the distal portion of the cylindrical body, the second diameter being smaller than the first diameter.

4. The suture anchor of claim 1, further comprising a receptacle defined at the proximal end of the elongated cylindrical body, the receptacle configured for receiving an installation tool for driving the suture anchor into the bone.

5. The suture anchor of claim 4, wherein the receptacle has a cross-sectional shape selected from a group consisting of circular, triangular, hexagonal, polygonal and cross-shaped.

6. The suture anchor of claim 4, wherein at least a portion of the receptacle includes internal threads for receiving a threaded portion of the installation tool.

7. The suture anchor of claim 1, wherein the distal tip of the anchor is interchangeable.

8. An anchor delivery system comprising the anchor according to claim 1, and an installation tool comprising a handle and a drive shaft extending from the handle, the drive shaft configured for engaging with the receptacle.

9. The system of claim 8, further comprising at least one stay-suture connected to the anchor and the installation tool, the stay-suture configured to retain the anchor in operative engagement with the drive shaft of the installation tool.

10. The system of claim 9, wherein the handle further comprises at least one suture holder for holding one or more free ends of the at least one stay-suture received by the transverse bore.

11. The system of claim 8, wherein at least a portion of the drive shaft includes external threads for engaging a portion of a receptacle having internal threads, the receptacle defined at a proximal end of the elongated cylindrical body.

12. A method for securing a suture to bone without tying a knot, the method comprising:
   partially driving a suture anchor into bone including driving a distal portion of the suture anchor defining a transverse bore into bone and driving at least one discontinuous rib of the anchor into bone, the at least one discontinuous rib being circumferentially formed around the anchor closer to a proximal end of the anchor than the transverse bore, the at least one discontinuous rib having at least one notch defining a longitudinal channel, the longitudinal channel extending proximally from the transverse bore through a portion of an outer surface of the anchor;
   sliding at least one suture threaded through the transverse bore to a desired position via the longitudinal channel;
   engaging the at least one suture with a cleat defining a narrow opening or slot configured to engage the at least one suture within the narrow opening or slot, wherein the cleat is positioned along a length of the longitudinal channel adjacent to the transverse bore; such that engaging the cleat with the at least one suture arrests a slidable motion of the at least one suture; and
   driving the anchor further into bone including driving at least one continuous rib continuously encircling the anchor into bone to fix the anchor into the bone and to compress the suture between the bone and the at least one continuous rib securing the suture to the bone.

13. The method of claim 12, wherein the steps of driving the anchor into bone comprise:
   engaging a distal end of an installation tool with a proximal end of the anchor; and
   pounding the installation tool to drive the anchor into bone.

14. The method of claim 13, wherein the anchor is retained in operative engagement with the installation tool prior to driving the anchor into bone by way of at least one stay-suture connected to the anchor and the installation tool.

15. The method of claim 12 further comprising selecting an appropriate distal tip of the anchor based on whether a hole is pre-formed in the bone.

16. A method for securing a suture to bone without tying a knot, the method comprising:
   partially driving a suture anchor into bone including driving a distal portion of the suture anchor defining a transverse bore into bone and driving at least one discontinuous rib of the anchor into bone, the at least one discontinuous rib being circumferentially formed around the anchor closer to a proximal end of the anchor than the transverse bore, the at least one discontinuous rib having at least one notch defining a longitudinal channel, the longitudinal channel extending proximally from the transverse bore through at least a portion of an outer surface of the anchor, wherein the longitudinal channel is in communication with the transverse bore;
   sliding at least one suture threaded through the transverse bore to a desired position via the longitudinal channel;
   engaging the at least one suture with a cleat defining a narrow opening or slot configured to engage the at least one suture within the narrow opening or slot, wherein engaging the cleat arrests a slidable motion of the at least one suture; and
   driving the anchor further into bone including driving at least one continuous rib continuously encircling the anchor into bone to fix the anchor into the bone and to compress the suture between the bone and the at least one continuous rib securing the suture to the bone, wherein the at least one continuous rib is closer to the proximal end than the at least one discontinuous rib.

17. The method of claim 16, wherein the steps of driving the anchor into bone comprise:
   engaging a distal end of an installation tool with a proximal end of the anchor; and
   pounding the installation tool to drive the anchor into bone.

18. The method of claim 16, wherein the step of engaging the at least one suture with the cleat further comprises pulling the at least one suture away from the distal end of the anchor.

* * * * *